US009623108B2

(12) United States Patent
Senin et al.

(10) Patent No.: US 9,623,108 B2
(45) Date of Patent: Apr. 18, 2017

(54) FORMULATION FOR ORAL ADMINISTRATION WITH BENEFICIAL EFFECTS ON THE CARDIOVASCULAR SYSTEM

(75) Inventors: Paolo Senin, Monza (IT); Ivo Setnikar, Milan (IT); Luigi Angelo Rovati, Monza (IT)

(73) Assignee: ROTTAPHARM S.p.A., Monza (IT)

( * ) Notice: Subject to any disclaimer, the term of this patent is extended or adjusted under 35 U.S.C. 154(b) by 1301 days.

(21) Appl. No.: 12/295,616

(22) PCT Filed: Mar. 29, 2007

(86) PCT No.: PCT/IB2007/051109
§ 371 (c)(1),
(2), (4) Date: Sep. 30, 2008

(87) PCT Pub. No.: WO2007/113748
PCT Pub. Date: Oct. 11, 2007

(65) Prior Publication Data
US 2009/0136469 A1 May 28, 2009

(30) Foreign Application Priority Data
Mar. 30, 2006 (IT) .............................. TO2006A0239

(51) Int. Cl.
| | | |
|---|---|---|
| *A01N 63/00* | (2006.01) | |
| *A61K 45/06* | (2006.01) | |
| *A61K 31/045* | (2006.01) | |
| *A61K 31/122* | (2006.01) | |
| *A61K 31/4741* | (2006.01) | |
| *A61K 31/519* | (2006.01) | |
| *A61K 36/05* | (2006.01) | |
| *A61K 36/06* | (2006.01) | |
| *A61K 36/29* | (2006.01) | |

(52) U.S. Cl.
CPC ............ *A61K 45/06* (2013.01); *A61K 31/045* (2013.01); *A61K 31/122* (2013.01); *A61K 31/4741* (2013.01); *A61K 31/519* (2013.01); *A61K 36/05* (2013.01); *A61K 36/06* (2013.01); *A61K 36/29* (2013.01)

(58) Field of Classification Search
CPC ................ A61K 31/045; A61K 31/122; A61K 31/4741; A61K 31/519; A61K 36/05; A61K 45/06; A61K 36/06; A61K 36/29; A61K 2300/00
USPC ....................................................... 424/93.51
See application file for complete search history.

(56) References Cited

U.S. PATENT DOCUMENTS

| | | | |
|---|---|---|---|
| 5,952,393 A | 9/1999 | Sorkin, Jr. | |
| 6,541,006 B1 | 4/2003 | Yegorova | |
| 2008/0102082 A1* | 5/2008 | Senin et al. | 424/195.16 |

FOREIGN PATENT DOCUMENTS

| | | |
|---|---|---|
| EP | 1 827 136 B1 | 6/2008 |
| WO | 02/094221 A1 | 11/2002 |
| WO | 03020260 A1 | 3/2003 |
| WO | 2006/029577 A1 | 3/2006 |
| WO | 2006/037725 A1 | 4/2006 |
| WO | 2006037725 A1 | 4/2006 |

OTHER PUBLICATIONS

Keith et al., Multicomponent therapeutics for networked systems. Nat. Rev. Drug Discovery, 2005, vol. 4: 1-8.*
Kong et al., Berberine is a novel cholesterol-lowering drug working through a unique mechanism distinct from statins. Nat. Med., 2004, vol. 10 (12): 1344-1351.*
Ivo Setnikar, et al., "Antiatherosclerotic Efficacy of Policosanol, Red Yeast Rice Extract and Astaxanthin in the Rabbit", Arzneimittel-Forschung / Drug Research, 2005, pp. 312-317, vol. 55, No. 6.
Arrigo F. G. Cicero, et al., "Eulipidemic Effects of Berberine Administered Alone or in Combination with Other Natural Cholesterol-lowering Agents", Arzneimittel-Forschung / Drug Research, 2007, pp. 26-30, vol. 57, No. 1.
Ioanna Gouni-Berthold, et al., "Policosanol: Clinical pharmacology and therapeutic significance of a new lipid-lowering agent," American Heart Journal, 2002, pp. 356-365, vol. 143, No. 2.
William B. Kannel, et al., "Cholesterol in the Prediction of Atherosclerotic Disease," Annals of Internal Medicine, Jan. 1979, pp. 85-91, vol. 90, No. 1.
Lynn P. Lowe, et al., "Impact of Major Cardiovascular Disease Risk Factors, Particularly in Combination, on 22-Year Mortality in Women and Men," Arch Intern Med, Oct. 12, 1998, pp. 2007-2014, vol. 158.
Roberto Menendez, et al., "Policosanol Modulates HMG-CoA Reductase Activity in Cultured Fibroblasts," Archives of Medical Research, 2001, pp. 8-12, vol. 32.
A. F. G. Cicero, et al., "A Dietary Aid from Active Natural Products: A Pilot Clinical Study on Lipid Profile," Br J Sports Med, 2006, p. 887, vol. 40.
Knud Lockwood, et al., "Progress on Therapy of Breast Cancer with Vitamin $Q_{10}$ and the Regression of Metastases," Biochemical and Biophysical Research Communications, Jul. 6, 1995, pp. 172-177, vol. 212, No. 1.
R Menendez, et al., "Policosanol inhibits cholesterol biosynthesis and enhances low density lipoprotein processing in cultured human fibroblasts," Biol Res, 1994, pp. 199-203, vol. 27.
Roberto Menendez, et al., "Effect of policosanol on the hepatic cholesterol biosynthesis of normocholesterolemic rats," Biol Res, 1996, pp. 253-257, vol. 29.
Roberto Menendez, et al., "Effects of policosanol treatment on the susceptibility of low density lipoprotein (LDL) isolated from healthy volunteers to oxidative modification in vitro," Br J Clin Pharmacol, 2000, pp. 255-262, vol. 50.

(Continued)

Primary Examiner — Ganapathirama Raghu

(57) ABSTRACT

Formulation for oral administration, in the form of tablets or of powder for extemporaneous use, able to exert a beneficial effect on the cardiovascular system and having eulipidaemic activity, cholesterol-lowering and triglyceride-lowering activity, antioxidant activity, and a protective action on the vasal endothelium, comprising berberine in combination with a policosanol and/or red yeast and preferably containing an antioxidant, such as astaxanthin and/or folic acid.

17 Claims, No Drawings

(56) References Cited

OTHER PUBLICATIONS

Monographie Berberis vulgaris (Berberitze). Bundesanzeiger, 1989, 43, 2.03.
Liliana Grigore, et al., "Armolipid, A Nutritional Supplement, Effectively Reduces Plasma Total and LDL Cholesterol in Moderate Hypercholesterolemia," Drugs Affecting Lipid Metabolism Meeting, Venice, Oct. 24, 2004-Oct. 27, 2004.
Miguel Benitez, et al., "A Comparative Study of Policosanol Versus Pravastatin in Patients with Type II Hypercholesterolemia," Current Therapeutic Research, Nov. 1997, pp. 859-867, vol. 58, No. 11.
Lisa M. Schwartz, et al., "Changing Disease Definitions: Implications for Disease Prevalence: Analysis of the Third National Health and Nutrition Examination Survey, 1988-1994," Effective Clinical Practice, Mar./Apr. 1999, pp. 76-84, vol. 2, No. 2.
Guy De Backer, et al., Executive Summary of "European guidelines on cardiovascular disease prevention in clinical practice," European Heart Journal, 2003, pp. 1601-1610, vol. 24.
The Italian Cardiovascular Epidemiological Observatory, Ital Heart J, 2004, pp. 49S-92S, vol. 5, suppl. 3.
Tamami Iwamoto, et al., "Inhibition of Low-Density Lipoprotein Oxidation by Astaxanthin," Journal of Atherosclerosis and Thrombosis, 2000, pp. 216-222, vol. 7, No. 4.
Daniel Steinberg, "Low Density Lipoprotein Oxidation and Its Pathobiological Significance," The Journal of Biological Chemistry, 1997, pp. 20963-20966, vol. 272, No. 34.
Christopher T. Sempos, et al., "Prevalence of High Blood Cholesterol Among US Adults," JAMA, Jun. 16, 1993, pp. 3009-3014, vol. 269, No. 23.
Carol J. Boushey, et al., "A Quantitative Assessment of Plasma Homocysteine as a Risk Factor for Vascular Disease," JAMA, Oct. 4, 1995, pp. 1049-1057, vol. 274, No. 13.
A. Endo, "Chemistry, Biochemistry, and Pharmacology of HMG-CoA Reductase Inhibitors," Klin Wochenschr, 1988, pp. 421-427, vol. 66.
K. Lockwood, et al., "Apparent Partial Remission of Breast Cancer in 'High Risk' Patients Supplemented with Nutritional Antioxidants, Essential Fatty Acids and Coenzyme Qio," Molec. Aspects Med., 1994, pp. s231-s240, vol. 15 (supplement).
Ricky Y.K. Man, et al., "Cholestin inhibits cholesterol synthesis and secretion in hepatic cells (HepG2)," Molecular and Cellular Biochemistry, 2002, pp. 153-158, vol. 233.
Weijia Kong, et al., "Berberine is a novel cholesterol-lowering drug working through a unique mechanism distinct from statins," Nature Medicine, Dec. 2004, pp. 1344-1351, vol. 10, No. 12.
Roberto Menendez, et al., "Oral Administration of Policosanol Inhibits In Vitro Copper Ion-Induced Rat Lipoprotein Peroxidation," Physiology & Behavior, 1999, pp. 1-7, vol. 67, No. 1.
Karl Folkers, et al., "Lovastatin decreases coenzyme Q levels in humans," Proc. Natl. Acad. Sci. USA, Nov. 1990, pp. 8931-8934, vol. 87.
Richard A. Willis, et al., "Lovastatin decreases coenzyme Q levels in rats," Proc. Natl. Acad. Sci. USA, Nov. 1990, pp. 8928-8930, vol. 87.
Charles C. Thomas, "Cureton K. The physiological effects of wheat germ oil in humans," Exercise, Springfield, IL—USA, 1972.
Astaxanthin Accumulation in the Green Alga *Haematococcus pluvialis*, Sammy Boussiba and Avigad Vonshak, received Apr. 22, 1991; Accepted, Aug. 6, 1991.
Cholesterol-lowering effects of a proprietary Chinese red-yeast-rice dietary supplement; David Heber, et al. Am. J. Clin. Nutr. 1999, 69:231-6.
Inhibition of Low-Density Lipoprotein Oxidation by Asataxanthin, Iwamoto, et al; Journal of Atheroscierosis and Thrombosis, vol. 7, No. 4, pp. 216-222.
A Comparative Study of Policosanol Versus Pravastatin in Patients With Type II Hypercholesterolemia, Benitez, et al.; Cuttent Therapeutic Research, vol. 58, No. 11, Nov. 1997; 001-393X/97, pp. 859-867.
Polisosanol inhibits cholesterol biosynthesis and enhances low density lipoprotein processing in culures human fibroblasts; Menendez, et al., Biol Res: 27: 199-203 (1994).
Effect of Policosanol on the Hepatic Cholesterol Biosynthesis of Normocholesterolemi Rats, Roberto Menendez, et al. Centro de Prouctios Naturales, Centro Nacional de Investigaciones Cientificas, La Habana, Cubs, Biol, Res. 29: 253-267 (1996).
Original Article: Policosanol Modulates HMG-CoA Reductase Activity in Cultured Fibroblasts, Menendez, et al.; Jul. 22, 1999, Archives of Medical Research 32 (2001) 8-12.
Oral Administration of Policosanol Inhibits In Vitro Copper Ion-Induced Rat Lipoprotein Peroxidation, Menendez, et al., Pharacology Department, Center of Natural Products, National Center for Scientific Research; Physiology & Behavior, vol. 67, No. 1, pp. 1-7, 1999.
Effectsof Policosanol Treatment on the Susceptibility of Low Density Lipoprotein 9LDL) Isoldated From Healthy Volunteers to Oxidative Modification in Vitr, Menendez; et al., Center of Natural Products, National Center for Scientific Research, Jun. 25, 1999, pp. 255-262.
Low Density Lipoprotein Oxidation and Its Pathobiological Signficance, The Journal of Biological Chemistry, vol. 272, No. 34, Issue of Aug. 22, pp. 20963-20966, 1997.
Chemistry, Biochemistry, and Pharacology of HMG-CoA Reductase Inhibitors, A. Endo, Klinische Wochen Schrift, Springer-Verlag 1988; 421-427.
Cholestin Inhibits Cholesterol Synthesis and Secretion in Hepatic Cells (HepG2); Ricky Y.K. Man, et al., Received Sep. 7, 2001; accepted Feb. 8, 2002; Molecular and Cellular Biochemistry 233: 153-158, 2002.
Apparent Partial Remission of Breast Cancer in "High Risk" Patients Supplemented With Nutritional Antioxidants, Essential Fatty Acids and Coenzyme Q10; Lockwood, et al.; Moltec. Aspects Med. vol. 15 (Supplementl), pp. S231-s240, 1994.
Progress on Therapy of Breast Cancer With Vitamin Q10 and the Regression of Metastases, Lockwood, et al.; Pharma Nord, Institute for Biomedical Research, University of Texas at Austin, Austin, Texas 78712, vol. 212, No. 1, 1995, Jul. 6, 1995.
Lovastatin Decreases Coenzyme Q levels in Rats, Willis, et al., Proc. Nat. Accud. Sci, USA, vol. 87, pp. 8928-8930, Nov. 1990, Medical Sciences.
Lovastatin Decreases Coenzyme Q levels in Humans, Folkers, et al., Proc. Natl. Accud. Sci. USA, vol. 87, pp. 8931-8934, Nov. 1990, Medical Sciences.
Oxygen Free Radicals and Hypercholesterolemic Atherosclerosis: Effect of Vitamin E; Prasad, et al., Atherosclerosus Experimental, 1993.
Experiemental Atherosclerosis and Oxygen Free Radicals; Prasad, et al.; The Journal of Vascular Diseases; Sep. 1989.
Technics for Stuying Atherosclerotic Lesions, Holman, et al. Study of Atherosclerotic Lesions, vol. 7, No. 1., 1956, pp. 42-47.
Search Report of WO 2006037725, published Apr. 13, 2006; Rottapharm S.p.A.

\* cited by examiner

FORMULATION FOR ORAL ADMINISTRATION WITH BENEFICIAL EFFECTS ON THE CARDIOVASCULAR SYSTEM

CROSS REFERENCE TO RELATED APPLICATION

This application is a National Stage of International Application No. PCT/IB2007/051109 filed Mar. 29, 2007, claiming priority based on Italian Patent Application No. TO2006A000239, filed Mar. 30, 2006, the contents of all of which are incorporated herein by reference in their entirety.

The present invention relates to a formulation for oral administration, in the form of tablets or of powder for extemporaneous use, which is able to exert a beneficial effect on the cardiovascular system, owing to a combination of activities such as eulipidaemic, cholesterol-lowering and triglyceride-lowering, antioxidant and protective of the vasal endothelium and others connected with these directly or indirectly.

In the industrialized countries, cardiovascular diseases are among the main causes of death for men and women [Schwarz et al. 1999, Lowe et al. 1998, Sempos et al. 1993] and in this connection, extensive epidemiological studies have identified the conditions that predispose to cardiovascular diseases, i.e. the so-called "risk factors" which can be classified as "unalterable" (genetic, sex, age) and "alterable". The alterable factors are mainly metabolic factors (for example hypercholesterolaemia, hypertriglyceridaemia, hyperfibrinogenaemia, hyperhomocysteinaemia, diabetes mellitus, visceral obesity), biological factors (for example arterial hypertension) and factors connected with lifestyle (smoking, incorrect eating habits, sedentary lifestyle, etc.).

Many cardiovascular diseases are of an arteriosclerotic nature, i.e. are due to narrowing of the lumen of the arteries owing to the deposition of cholesterol, calcium and fibrin in the vessel wall, or to occlusion of the arteries caused by a thrombus that formed from an atheromatous plaque. As was documented in the Framingham epidemiological study [Kannel et al. 1995], the incidence and the severity of arteriosclerosis are closely related to the cholesterol level in the blood and especially when low-density lipoproteins (LDL), or "bad" cholesterol, exceed values of 160 mg/dl [Ministry of Health 2003]. In fact it is now generally agreed that coronary pathology might be effectively prevented by maintaining plasma cholesterol at levels below 190 mg/dl. There are, however, relatively few adults who have a blood cholesterol level below the aforementioned limit. A study conducted by the Italian Cardiovascular Epidemiological Centre [2004] shows that in fact 6 out of 10 Italians have a cholesterol level above the aforesaid threshold.

It is therefore very important to keep blood cholesterol under control, as is also recommended by the "European guidelines on cardiovascular prevention" [2003]. In practice, if there is mild or moderate hypercholesterolaemia (blood cholesterol between 190 and 250 mg/dl), a change of lifestyle is required, adopting a healthy diet, low in saturated fats and rich in fruit and vegetables, with a calorie intake adjusted to the individual's needs. It is also necessary to eliminate unnecessary risk factors, especially smoking, and ensure adequate physical activity every day.

These are simple rules but they are not easy to follow in present living conditions. Dietary supplements that act as adjuvants in the control of plasma cholesterol can therefore provide useful support, in conjunction with a generally adequate diet.

Another important cardiovascular risk factor is represented by raised levels of triglycerides (above 150-200 mg/dl), especially if accompanied by a reduced HDL cholesterol level (<40 mg/dl) or within the so-called "metabolic syndrome".

Another pathogenetic factor of arteriosclerosis is peroxidation of LDL. In fact LDLs are transported in the blood without particular pathological problems. However, if they are peroxidized by ROS (Reactive Oxygen Species), they pass through the endothelium of the arteries and are captured and stored by macrophages. The latter, packed with peroxidized LDL, are transformed to so-called "foam cells", which represent the initial nucleus of atheromas of the intima, from which arteriosclerotic plaques then form. Antioxidants that inhibit the peroxidation of LDL are therefore very useful for preventing arteriosclerosis. This objective can be achieved with an appropriate choice of foods and with the support of suitable dietary supplements rich in antioxidants.

Then there are other metabolic factors of cardiovascular risk, among which we should certainly mention homocysteine, which is an atherogenic and thrombogenic agent. Increase in plasma homocysteine (hyperhomocysteinaemia) represents an independent risk factor for diseases of coronary, cerebral or peripheral vascular origin, or originating from deep vein thrombosis [Longo 2001]. The relation between hyperhomocysteinaemia, i.e. blood homocysteine above 10 µmol/l, and increased cardiovascular risk was examined and demonstrated in a thorough meta-analysis carried out on 27 controlled prospective clinical studies [Boushey et al. 1995]. It is therefore necessary to avoid hyperhomocysteinaemia, for example with the administration of B-group vitamines and in particular folic acid.

In conclusion, a correct lifestyle, adequate nutrition and the use of suitable dietary supplements are sufficient in most cases for controlling the cholesterol level in the blood when this is slightly or moderately raised. Dietary supplements are also useful in subjects with "intermediate" overall risk, or those having a probability between 10% and 20% of developing a cardiovascular disease in the next 10 years of life, but for whom therapy with cholesterol-lowering drugs is not yet justified, although it is still recommended to lower the blood cholesterol level to below the threshold of 190 mg/dl.

There are at present various dietary supplements that can provide beneficial action and give a significant reduction of cardiovascular risk, especially if combined with a controlled diet and with healthy physical activity.

A scientific work was published recently [Setnikar et al. 2005], subsequent to an Italian patent application [application TO2004A000682] filed by the authors of the present application, which describes a composition for oral administration based on policosanol, red yeast (RY) and an antioxidant selected from astaxanthin and folic acid (designated hereinafter as Ass), the eulipidaemic efficacy of which clearly follows from the pharmacological results described herein.

Ass, however, displays relatively low efficacy on blood triglycerides which, as already emphasized, represent in their turn an important cardiovascular risk factor. In this connection, to obtain significant triglyceride-lowering effects, normally nicotinic acid or PUFA (polyunsaturated fatty acids) are used. However, both must be used at very high doses which lead to unpleasant and undesirable side effects.

The present invention is based on the development of a composition for oral administration in which an active principle that has effective and demonstrable triglyceride-lowering action and at the same time does not have the undesirable side effects of nicotinic acid and of PUFA, is added to Ass. The choice fell on berberine, a natural substance of vegetable origin whose triglyceride-lowering and cholesterol-lowering activities were recently documented clinically [Kong et al. 2004]. The synergistic effect of the combination of berberine with Ass, designated COMB hereinafter, and an object of the present patent application, was evaluated experimentally on hypertriglyceridaemic and hypercholesterolaemic rabbits, with extraordinarily positive experimental results and indeed above any expectation, as can be seen later in the detailed experimental section.

The invention thus relates to a composition for oral administration as defined in the claims that follow.

The properties of the various active components of COMB, the object of the present invention, together with those of other potential synergists such as folic acid and coenzyme Q10, are described hereunder.

Berberine

Berberine is a natural vegetable preparation extracted from the bark of *Berberis aristata*, a spiny shrub originating from the Himalayas and Nepal, belonging to the Berberidaceae family.

Chemistry

Chemically berberine is 5,6-dihydro-9,10-dimethoxybenzo[g]-1,3-benzodioxolo[5,6-a]quinolizinium, with the empirical formula $C_{20}H_{18}NO_4^+$ and molecular weight 336.37.

Berberine is obtained from the bark of *Berberis aristata* by aqueous-alcoholic extraction and then crystallization, processes which leave the chemical structure of the molecule unchanged, whereas microbial contamination is kept within the limits stipulated by the European Pharmacopoeia for pharmaceutical use.

Eulipidaemic Effect

Berberine is used traditionally for its antimicrobial action in infectious diarrhoea, in urinary tract infections and for local treatment of wounds and ulcers. In addition it has immunostimulant, antipyretic and antihaemorrhagic action [Leung et al. 1989] [Monograph 1989].

A controlled clinical study on 91 hypercholesterolaemic patients, 63 of whom were treated for 3 months b.i.d. with 500 mg of berberine, and 28 with placebo, was published just recently [Kong et al. 2004]. The patients treated with berberine showed a significant decrease of 29% in total cholesterol (2% with placebo), 25% in low-density lipoproteins (LDL) (0% with placebo) and 35% in triglycerides (5% with placebo). HDL, in contrast, remained unchanged.

Another controlled study was conducted on 20 patients who had hypercholesterolaemia and hypertriglyceridaemia, administering 500 mg of berberine in a single dose once a day [Cicero et al. 2006]. Berberine reduced total cholesterol by 16%, LDL by 20% and triglycerides by 22%. All these changes were found to be statistically highly significant ($p<0.0001$). Moreover, HDL ("good" cholesterol) increased by 7% ($p<0.05$). The treatment was well tolerated and hepatic transaminases were improved.

These two clinical studies demonstrate that berberine exerts an effective eulipidaemic spectrum on various blood lipids and suggest that it can be used in the prevention of cardiovascular risks connected with atherosclerotic manifestations.

The eulipidaemic action of berberine was further confirmed on hamsters fed a diet enriched with cholesterol and fats, which caused a large increase in blood levels of total cholesterol, LDL and triglycerides [Kong et al. 2004]. Treatment with 50 and with 100 mg/kg/d of berberine for 10 days significantly reduced, by 25% and 38% respectively, the increase in total cholesterol caused by the hyperlipidic diet and, by 26% and 41% respectively, the increase in LDL.

Mechanism of Action

Investigation of the molecular mechanism of action showed that berberine increases, in the liver, mRNA and the LDL receptor (LDLR) protein, involving an extracellular signal-regulated kinase (ERK). Furthermore, berberine stabilizes the LDLR and prolongs its half-life. With these mechanisms, berberine causes a notable increase in LDLRs located on the membrane of the hepatocytes, promoting endocytosis of the LDLs and hence their metabolic elimination. The mechanism by which berberine reduces the blood LDL is therefore different and independent of that of the statins, which act by inhibiting the endogenous synthesis of cholesterol from mevalonate by antagonizing 3-hydroxy-3-methylglutaryl-coenzyme A (HMG-CoA) reductase.

One interesting result of this study is the ability of berberine to lower the triglyceride level and therefore exert an overall eulipidaemic action.

Another interesting result is the decrease in hepatic transaminases in the patients treated with berberine 500 mg b.i.d.

In animals fed with the hyperlipidic diet, moreover, berberine is able to reduce the hepatic steatosis caused by the hyperlipidic diet.

Posology

The daily dose used in the invention is preferably 250-1000 mg (usually 500 mg), preferably taken after the evening meal.

Policosanol

Chemistry

"Policosanol" is the generic name given to a mixture of saturated long-chain ($C_{22}$-$C_{36}$) primary aliphatic alcohols, in the form of a solid, of waxy consistency, sparingly soluble in $H_2O$. The alcohols of which it is composed occur in the natural state in beeswax (from *Apis mellifera*), in the waxy matrix of sugar cane (*Saccharum officinarum*), in rice bran (*Oryza sativa*) and in various other plants.

The policosanol used in the present invention, in contrast to that normally obtained with the conventional wet processes which do not guarantee its purity and the total removal of the organic solvents employed in the extraction process, is preferably extracted by means of carbon dioxide in the supercritical state at extremely low temperature in the liquid phase.

This process guarantees its purity, conservation of the original chemical structure, total absence of organic solvents and preservation of the original proportions of the alcohols naturally present in the starting product.

Eulipidaemic Effect

Numerous clinical and experimental studies have documented the eulipidaemic action of policosanol, which is especially evident in subjects with hypercholesterolaemia. The effect is most noticeable on cholesterol associated with low-density lipoproteins (LDL-C) with inhibition of the synthesis of the cholesterol itself and increase in its elimination [Menendez et al. 1994, Menendez et al. 1996, Menendez et al. 2001].

Investigations into the mechanism of action of policosanol provide evidence of inhibition of the biosynthesis of cholesterol in a stage that is positioned between utilization of the acetate and production of the mevalonate, but excluding a direct effect on 3-hydroxy-3-methylglutaryl coenzyme A reductase (HMGCoA-r) [Menendez et al. 1996, Menendez et al. 2001] on which other well-known cholesterol-lowering agents act, for example the statins.

Policosanol, moreover, increases significantly, and in a dose-dependent manner, the binding and hepatic uptake of the LDLs, with a consequent positive acceleration of their catabolism [Menendez et al. 1994]. For policosanol, an action on the intestinal mucosa has also finally been proposed, relating to the absorption and intracellular metabolism of food lipids [Goumi-Berthold et al. 2002].

Inhibition of LDL Peroxidation

Various studies in vitro and in vivo have demonstrated that policosanol exerts an antioxidant action with consequent inhibition of the peroxidation of LDLs and of VLDLs (very low density lipoproteins) [Menendez et al. 1999]. Blocking of the peroxidation of LDLs, also confirmed by human clinical trials [Menendez et al. 2000], leads to an important antiatherogenic effect, because the LDLs only exert their atherogenic action in the oxidized state. This is in fact a necessary structural condition so that the LDLs can filter through the endothelium of the arteries to be captured by the receptor for the scavengers of the macrophages. The macrophages filled with peroxidized LDLs are transformed into "foam cells", the first step in the formation of atheromatous plaques.

Endothelial Protection

Policosanol protects the vasal endothelium from damage caused by mechanical and chemical agents [Benitez et al. 1997]. This endothelial damage leads to loss of membrane elasticity and an increase in permeability, which among other things promotes passage of the LDLs from the blood to the intima of the artery, with resultant formation of atheromatous plaques.

Pro-Energetic Action

Clinical research conducted since the 1950s has demonstrated that the use of policosanol brings beneficial effects on resistance to stress and to fatigue. This action involves the bioavailability of muscle glycogen, nerve reaction times, resistance to stress from hypoxia, the oxygen debt and, not least, the blood cholesterol level [Cureton 1972].

Policosanol is therefore used by athletes and sports people in general for its pro-energetic effect, which would be reflected in its role of "intracellular vehicle" for the essential fatty acids and for the other energy sources of the cell.

Posology

The daily dose used within the scope of the invention is preferably 5-40 mg (usually 10-20), preferably taken with the evening meal to obtain optimum absorption of the fatty alcohols. To be effective, the duration of treatment should be extended to at least six weeks.

Red Yeast (RY)

Chemistry

RY, or fermented red rice, is the product of fermentation of rice by a fungus, *Monascus purpureus*, which produces various substances, including a red pigment (whence the name "red yeast"), bacteriostatic agents and substances that modulate the level of lipids in the blood.

The latter are in fact the most interesting components for their beneficial effect on health. They are identified with the name "monacolines". The monacoline that is most effective for eulipidaemic purposes is monacoline K [Endo 1988] the content of which in RY depends on the strain of *Monascus purpureus* used and the fermentation conditions.

The RY used in the formulation that is the object of the present invention is preferably obtained in standardized fermentation conditions, with a particular strain of *Monascus purpureus*, selected for an optimum yield of monacoline K and a defined and titrated content of said active principle.

Eulipidaemic Effect

The blood cholesterol level is the sum of that ingested with food and of that arising from endogenous biosynthesis in the liver. This synthesis starts out from acetyl coenzyme A, from which 3-hydroxy-3-methylglutaryl coenzyme A (HMG-CoA) forms, and then, with the intervention of HMG-CoA reductase (HMG-CoA-r), mevalonate. Mevalonate is the key intermediate for the next stages of the cascade in the biosynthesis of cholesterol and represents the critical, limiting step for the endogenous production and consequent blood levels of cholesterol itself and of the LDLs.

Monacoline K competes structurally at the level of HMG-CoA-r with HMG-CoA, the mevalonate precursor, and has an activity for the enzyme 2000 times greater than that of the natural substrate, therefore giving rise to a mechanism of "competitive enzymatic inhibition" which impedes the biosynthesis of cholesterol [Man et al. 2002].

Posology

The daily dose of RY used within the scope of the invention is preferably the equivalent of an amount of monacoline between 1 and 6 mg, and preferably does not exceed the equivalent of 3 mg of monacoline in the compositions for use as nutritional supplement according to the invention.

Folic Acid (FA)

Chemistry

FA comprises a combination of three molecules: glutamic acid, p-aminobenzoic acid and a derivative of pteridine.

Our body is not able to synthesize FA and we are therefore dependent on food sources that are rich in it, such as leafy vegetables, liver, eggs and legumes. The daily requirement for FA, recommended for adults, is 0.2 mg and increases to 0.4 mg in pregnancy and to 0.3 mg during lactation.

Hyperhomocysteinaemia Correcting Effect

FA performs an essential role in many biological functions, such as synthesis of the nucleic acids DNA and RNA, the production and development of the red blood cells, proper development of the embryo in pregnancy, improvement of trophism and of the health of the skin, the stimulation of milk secretion, regulation of iron metabolism etc.

Moreover, FA corrects hyperhomocysteinaemia, a cardiovascular risk factor only a little less important than that of hypercholesterolaemia for coronary, cerebral and peripheral vascular diseases and for deep vein thrombosis [Longo 2001]. The action of FA is connected with its property as a donor of methyl groups which convert homocysteine to L-methionine and S-adenosylmethionine, removing excess homocysteine in the blood.

Posology

The dosage forms of the invention are preferably arranged for the administration of folic acid at daily doses from 0.1 to 0.6 mg, and more preferably from 0.15 to 0.4 mg.

Astaxanthin (Ast)

Chemistry

Ast is a reddish-orange pigment present in many living beings and especially in aquatic animals. Chemically it is a xanthophyll, belonging to the carotenoid family, of formula 3,3'-dihydroxy-β,β'-carotene-4,4'-dione and with two chiral centres on the two cyclic carbon atoms (3 and 3') bound to the hydroxyls.

The hydroxyls are important because they function as a docking point for other molecules, such as plasma proteins and lipoproteins, and because they impart a bipolar character to Ast. Ast is thus able to form hydrogen bonds with the polar sites present on the inside and outside of the phospholipid double layer that forms the cell membrane, being disposed transversely to said membrane.

Ast can therefore capture and inactivate the free radicals which attack cells from the outside and those attacking them from the inside, efficiently protecting tissues from damage caused by free radicals and in general against all agents with an oxidizing action.

Owing to its structural characteristics, Ast displays antioxidant activity four times greater than that of lutein, ten times greater than that of β-carotene and actually from a hundred to a hundred and fifty times greater than that of vitamin E.

The Ast used in the formulation of the present invention is preferably an extract obtained from an alga, *Haematococcus pluvialis*, by a special process that employs supercritical carbon dioxide and makes it possible to preserve the chemical structure of natural Ast and concentrate it to 2.5%, stabilizing it in a complex lipid matrix.

Antioxidant Effect

On account of its powerful antioxidant activity, Ast is able to exert a manifest protective action against oxidative stress, a known cause of ageing, of degenerative diseases of the nervous system and of tumours. Moreover, it can be used advantageously against irritative processes due to free radicals triggered by solar and ionizing radiation.

Ast is also used for protecting the structures of the retina, in particular for the treatment of macular degeneration. Other fields of potential interest for application, connected with the inactivation of free radicals, relate to detoxication after smoking, after an unbalanced diet through excess of fats, from environmental pollutants, etc.

Reduction of Cardiovascular Risk

Cardiovascular pathology is largely dependent on atherosclerotic phenomena and on thrombotic events. The formation of atheromatous plaques is closely correlated with the type and quantity of blood lipids and in particular LDL-cholesterol (LDL-C).

LDL-C is not dangerous in itself, but becomes so following its peroxidation by free radicals. In fact, peroxidation increases its affinity for the arterial walls, with consequent infiltration in the intima and capture by the macrophages, which degenerate to "foam cells", the first step in the process of formation of atheromatous plaques and of arteriosclerosis, a primary factor of cardiovascular risk (CVR) [Steinberg 1997].

It is actually by intervening in this mechanism that Ast, owing to its pronounced antioxidant activity, resists the peroxidation of LDL-C and its transformation to an atheromatous agent [Iwamoto et al. 2000].

Safety of Use

The NOAEL (No Observed Adverse Effect Level) for doses of Ast, repeated daily in an animal, is 1340 mg/kg, equivalent to more than 80 g in humans.

Posology

The dosage forms, according to the invention, preferably comprise astaxanthin in daily doses of 0.1-5 mg, and preferably from 0.4 to 2 mg, preferably taken with a meal, to promote its intestinal absorption.

Coenzyme Q10 (CoQ10)

CoQ10 is a substance of lipid character with a quinone-type structure. It is of wide occurrence in nature, including the human body, hence its alternative name "ubiquinone". The main function of CoQ10 is as a co-factor in the electron-transport chain in the series of oxidation-reduction reactions involved in the synthesis of ATP.

Because nearly all cellular functions depend on an adequate supply of ATP, CoQ10 is essential for all of our body's tissues and organs. It is normally synthesized in vivo, but there may be situations in which its endogenous production proves insufficient. In this case the deficiency of CoQ10 is felt by all cells and particularly by those that are metabolically most active, such as the cardiac cells, the cells of the nervous system and the cells of the immune system.

Deficiency of CoQ10 is therefore directly linked to a whole range of dysfunctions such as cardiovascular diseases, arterial hypertension and AIDS.

Indications

CoQ10 has proved useful in cardiovascular diseases because it improves the energy efficiency of the myocardium and of the vasal muscles. It has also been used with outstanding results in cancer therapy [Lockwood et al. 1994, Lockwood et al. 1995] and in the treatment of muscular dystrophy.

Recently, it has also been introduced in sports practice for improving athletes' energy efficiency and physical performance indices. Not least in importance is its antioxidant action, with consequent protection of cell structures against free radicals, on which, in synergy with vitamin E, CoQ10 exerts a protective action against damage from oxidative stress.

Interactions

The biosynthesis of CoQ10 requires HMGCoA reductase. Therefore substances that inhibit this enzyme, for example statins, might at very high doses produce a state of deficiency of CoQ10. Investigations conducted in rats and in humans in fact suggest that subjects with low basal levels of CoQ10 and sub-optimal cardiac functionality may develop a deficit of CoQ10 after taking inhibitors of HMG-CoA reductase [Willis et al. 1990, Folkers et al. 1990].

It is concluded from this that supplementation of CoQ10 is always useful in subjects undergoing treatment with inhibitors of HMG-CoA reductase, also and especially in subjects with CVR, because CoQ10 improves the energy efficiency of the myocardium and of the vasal muscles.

Posology

The daily dose of CoQ10 used in the present invention is preferably in the range of 1-20 mg, and preferably from 2 to 4 mg.

EXPERIMENTAL SECTION

The action of the active principles, according to the composition of COMB, was tested and evaluated experimentally on rabbits rendered hypercholesterolaemic and hypertriglyceridaemic with a diet with added cholesterol, powdered egg yolk and lard.

Doses Administered

Note: all the daily doses used in the treatment groups, described in the experimental section, are about 4 times higher than those stated in the examples of formulation described in a later section. An exception is the group treated with berberine 100 mg/kg, for which the dose of active principle corresponds to about 13 times that contained in the examples of formulations intended for oral administration in humans. This served for evaluating the synergistic effect of berberine, at a dose of 30 mg/kg, when combined with the other active principles under investigation. The difference in posology between animals and humans is perfectly normal in pharmacology, because it is well known that the pathologies induced experimentally in animals are always dramatically and unnaturally more severe than those that occur spontaneously in humans.

Animals

New Zealand White rabbits of 6-8 weeks and with body weight of 1.8-2.0 kg.

Feeding

The following feeds, in pellets, were provided at a ration of 150 g of feed per day. Water was available ad libitum.

STAND: Standard feed for guinea pigs and rabbits according to Sherman, in pellets (Laboratorio Dottori Piccioni S.n.c.).

ATER: Atherogenic feed, i.e. standard feed for guinea pigs and rabbits according to Sherman, in pellets (Laboratorio Dottori Piccioni S.n.c.) with addition of 10% powdered egg yolk, 10% lard and 1% cholesterol according to Kong et al. [2004].

Active Principles

Policosanol (Pol)

Policosanol is the generic name given to a mixture of saturated long-chain primary aliphatic alcohols, which are also called "fatty alcohols". The Pol used in the following experiments comprises 1-triacontanol with 30 carbon atoms (25-30%), 1-octacosanol with 28 carbon atoms (16-23%), 1-hexacosanol with 26 carbon atoms (5-15%) and lesser amounts of other fatty alcohols.

Red Yeast (RY)

A dry extract from rice fermented with *Monascus purpureus* standardized to 1.5% of monacoline was used.

Berberine (Berb)

A dry extract from *Berberis aristata* titrated at 90% berberine was used.

Astaxanthin (Ast)

A concentrate of extract from the product of fermentation with *Haematococcus pluvialis*, containing 2.5% astaxanthin, was used.

Association (Ass)

A homogeneous mixture containing 0.6 mg/kg of Pol, 0.18 mg/kg of monacoline and 0.03 mg/kg of Ast was prepared. This mixture corresponds qualitatively and quantitatively to that cited previously, identified as Ass and described in Italian patent application TO2004A00062.

Combination (COMB)

A mixture of Ass with addition of 30 mg/kg of berberine was prepared.

Administration

The substances under investigation were administered by stomach tube, once a day, suspended in 2 ml/kg of carboxymethylcellulose 0.2% (CMC).

Treatments and Groups

All the animals were acclimatized in the living quarters at $25\pm2°$ C. and relative humidity 55-65%. After 1 week, blood samples were taken in order to obtain the baseline data. The animals were then randomized to the following treatment groups of 10 rabbits each.

C: Controls with feed STAND and daily administration of 2 ml/kg of CMC by stomach tube.

AT: Controls with feed ATER and with daily administration of 2 ml/kg of CMC by stomach tube.

Ber30: Feed AT, with daily administration of berberine 30 mg/kg in 2 ml/kg of CMC, by stomach tube.

Ber100: Feed AT, with daily administration of berberine 100 mg/kg in 2 ml/kg of CMC, by stomach tube.

Ass (reference association (combination) for lowering blood lipid level): Feed AT, with daily administration of Ass in 2 ml/kg of CMC, by stomach tube.

COMB: Feed AT, with daily administration of Ass with addition of 30 mg/kg of berberine in 2 ml/kg of CMC, by stomach tube.

The treatments were continued for 3 months. Blood samples were taken for analysis after 1, 2 and 3 months.

Blood Analyses

Triglycerides

Total serum cholesterol

HDL-C

LDL-C

These analyses were carried out with suitably validated, conventional laboratory methods.

Statistical Analysis

A descriptive statistical analysis was performed using conventional methods of calculation.

Results

Total cholesterol (CT)

After 3 months, the atherogenic feed (AT) caused CT to increase from a baseline mean of $1.5\pm0.09$ mmol/l to $61.8\pm4.5$ mmol/l, i.e. 36 times the baseline level.

The administration of 30 mg/kg/d of berberine (Ber30) reduced, by 15% (not statistically significant), the increase in CT caused by AT.

The administration of 100 mg/kg/d of berberine (Ber100) reduced, by 87% ($p<0.001$), the increase in CT caused by AT.

The administration of Ass (Association) reduced, by 79% ($p<0.001$), the increase in CT caused by AT, i.e. a little less than the reduction observed with 100 mg/kg of berberine.

Finally, the administration of COMB (Ass with 30 mg/kg/d of berberine) reduced, by 94% ($p<0.001$), the increase in CT caused by AT. The reduction of the increase in CT induced by COMB was significantly greater ($p<0.05$) than that observed with Ber100 and with Ass. It is important to note that COMB made it possible to keep CT at blood levels just a little above the normal values found prior to administration of atherogenic feed.

The potentiation of the reduction in CT provided by 30 mg/kg/d of berberine added to Ass in COMB, which was actually greater than that induced by 100 mg/kg of berberine, is notable and unexpected; in contrast, 30 mg/kg of berberine was not able on its own to give a significant decrease in blood cholesterol.

Low-Density Lipoproteins (LDL)

After 3 months, the atherogenic feed (AT) produced an increase in LDL from a baseline mean of $0.71\pm0.04$ mmol/l to $56.8\pm3.3$ mmol/l, i.e. 80 times the baseline level.

The administration of 30 mg/kg/d of berberine (Ber30) reduced, by 13% (not statistically significant), the increase in LDL caused by AT.

The administration of 100 mg/kg/d of berberine (Ber100) reduced, by 89% ($p<0.001$), the increase in LDL caused by AT.

The administration of Ass (Association) reduced, by 84% ($p<0.001$), the increase in LDL caused by AT, i.e. a little less than the reduction observed with 100 mg/kg of berberine.

Finally, the administration of COMB (Ass with 30 mg/kg/d of berberine) reduced, by 96% ($p<0.001$), the increase in LDL caused by AT. The reduction of the increase in LDL induced by COMB was significantly greater ($p<0.001$) than that observed with Ber100 and with Ass. It is important to note that in this case too, COMB made it possible to keep LDL to blood levels only a little above the normal levels found prior to administration of atherogenic feed.

The potentiation of the reduction in LDL provided by 30 mg/kg/d of berberine combined with Ass in COMB is notable and unexpected. This effect was greater than that induced by 100 mg/kg of berberine, whereas 30 mg/kg of berberine was not able on its own to give a significant decrease in blood LDL. The results obtained for LDL are essentially similar, but much more pronounced, than those observed for CT.

High-Density Lipoproteins (HDL)

After 3 months the atherogenic feed (AT) produced a slight, though not significant, increase in HDL. The various treatments caused moderate absolute increases in HDL, which are difficult to quantify in percentage terms owing to the variability of the baseline levels. However, a decrease in HDL sufficient to cause us to fear an increase in atherogenic risk was never observed as a result of the treatments.

Blood Triglycerides (TG)

After 3 months the atherogenic feed (AT) caused an increase in TG from a baseline mean of 0.70±0.04 mmol/l to 9.63±0.36 mmol/l, which is 14 times the baseline level. Feed AT therefore induces a very pronounced increase in TG, above that of the cholesterols, and is accordingly suitable for investigating substances with possible triglyceride-lowering effect.

The administration of 30 mg/kg/d of berberine (Ber30) reduced, by 43% ($p<0.01$), the increase in TG caused by AT.

The administration of 100 mg/kg/d of berberine (Ber100) reduced, by 66% ($p<0.001$), the increase in TG caused by AT.

The administration of Ass (Association) reduced, by 27% (not statistically significant), the increase in TG caused by AT.

Finally, the administration of COMB (Ass with 30 mg/kg/d of berberine) reduced, by 76% ($p<0.001$), the increase in TG caused by AT. The reduction of the increase in TG induced by COMB was therefore even greater than that produced by Berb100, although not statistically significant.

In conclusion, in 3 months, feed AT, atherogenic and rich in fats, caused a large increase in TG. This increase is reduced significantly by berberine 30 mg/kg/d and even more by berberine 100 mg/kg/d. Ass did not have any significant effects on the increase in TG whereas Comb (in which 30 mg of berberine is added to Ass) causes a marked reduction of the increase in TG, actually greater than that encountered with berberine 100 mg/kg/d, showing surprisingly and unexpectedly, in COMB, a potentiation, by the "Association", of the triglyceride-lowering effect of berberine.

CONCLUSIONS

The cholesterol-lowering and triglyceride-lowering effects of the products under investigation were investigated on rabbits given a diet enriched with cholesterol and fats, which in 3 months of treatment caused a very pronounced increase in cholesterol and triglycerides in the blood. Together with the feed, the following products were administered daily by the oral route, for 3 months.

C (Controls): Just the excipient (2 ml/kg of carboxymethylcellulose 0.2% (CMC).

Berb30: Berberine 30 mg/kg/d in 2 ml/kg of CMC.

Berb100: Berberine 100 mg/kg/d in 2 ml/kg of CMC.

Ass: Association (i.e. combination) of 0.6 mg/kg of Pol, 0.18 mg/kg of monacoline and 0.3 mg/kg of Ast, suspended in 2 ml/kg of CMC.

COMB: Ass with addition of 30 mg/kg/d of berberine, suspended in 2 ml/kg of CMC.

The atherogenic, fatty diet increased total cholesterol (CT) by 36 times the baseline level, low-density lipoproteins (LDL) by 80 times, high-density lipoproteins (HDL) by 1.2 times and triglycerides (TG) by 14 times.

Berb30 reduced the increase in CT by 15%, the increase in LDL by 13% and the increase in TG by 43%. Berb30 also produced a significant increase of 0.48 mmol/l in HDL.

Berb100 reduced the increase in CT by 87%, the increase in LDL by 89% and the increase in TG by 66%. Berb100 also produced a significant increase of 0.53 mmol/l in HDL.

Ass reduced the increase in CT by 79%, the increase in LDL by 84% and the increase in TG by 27%. Ass also produced a significant increase of 0.48 mmol/l in HDL. As was to be expected, Ass was very effective in restricting the increases in CT and LDL, whereas its activity in controlling the increases in TG was relatively slight and actually much lower than that of the low dose of berberine alone.

COMB reduced the increase in CT by 94%, the increase in LDL by 96% and the increase in TG by 76%. COMB in addition produced a significant increase of 0.53 mmol/l in HDL.

The potentiation of the reductions of the increases in CT and LDL following addition of 30 mg/kg/d of berberine to Ass was unexpected and very substantial. In fact, these reductions were greater than those induced by 100 mg/kg of berberine, whereas 30 mg/kg of berberine on its own was not able to reduce CT and LDL significantly.

COMB also almost normalized TG and based on this parameter it was more effective even than Berb100.

Addition of 30 mg/kg/d of berberine to Ass, in COMB, thus induces a surprising and unexpected reducing effect on total cholesterol, on LDL and on triglycerides, bringing these blood parameters, increased as a result of the atherogenic diet, back to almost normal levels.

These results are undoubtedly also applicable to the case of human cardiovascular risk because the experimental model adopted reproduces its initial pathogenetic mechanism and because the doses of the various active principles, relative to body weight, are comparable to the recommended doses for humans, bearing in mind that the pathologies induced experimentally in animals are always dramatically more severe than those occurring spontaneously in humans.

Similar results in terms of synergism were obtained using, in the tests mentioned previously, a composition COMB corresponding to that mentioned above, but in which the Ast component was replaced with folic acid (0.012 mg/kg).

EXAMPLES

The formulations given below illustrate possible practical applications of the present invention and as such must not be considered as limiting in any way said invention.

Particular reference is made to the excipients of the forms considered, which can be used as alternatives to those explicitly mentioned in the present invention, depending on the technological and formulation requirements, and which can moreover be selected from a very wide range of products available on the market and well known to a person skilled in the art of pharmaceutics and therefore not requiring any inventive step.

Example 1

Tablets for Oral Use

The formulation presented below relates to active principles and excipients (with description of the corresponding technological function) that can be used in the preparation of tablets to be used for oral administration of the object of the present invention.

The daily dose of the active principles is incorporated in a single tablet whose preparation only requires normal operations that are well known to a person skilled in the art, namely:

Weighing of the individual components of the formulation.

Wet granulation, using aqueous solution of polyvinylpyrrolidone K-25, of berberine, RY and pregelatinized starch (granules A) in a suitable granulator.

Drying of granules A in an air-circulating stove at a temperature not above 50° C. and to constant weight (any other type of drying can be used provided it is validated beforehand).

Sieving of granules A and of the other components of the formulation.

Preparation of the Compression Mixture by Homogenization of Granules A with the Other components of the formulation in a suitable mixer.

Compression of the resultant mixture in a suitable automatic tablet press, finally obtaining tablets having shape and dimensions compatible with the route of administration.

| Active principles | Quantity/tablet |
|---|---|
| Berberine dry extract[*] | 550 mg |
| (Corresponding to berberine) | (500 mg) |
| RY[**] | 200 mg |
| (Corresponding to monacoline K) | (3 mg) |
| Extract of microalgae[***] | 20 mg |
| (*Haematococcus purpureus*, corresponding to astaxanthin) | (0.5 mg) |
| Policosanol | 10 mg |
| Coenzyme Q10 | 2 mg |
| Folic acid | 0.2 mg |

[*]Contains 90% berberine
[**]Rice fermented with *Monascus purpureus* containing 1.5% of monacoline K
[***]Contains 2.5% astaxanthin

| Excipients | Quantity/tabl. | Function |
|---|---|---|
| Pregelatinized starch[*] | 200 mg | Binder/Diluent |
| Polyvinylpyrrolidone K-25[*] | 30 mg | Binder |
| Microcrystalline cellulose[**] | q.s. | Diluent/Disintegrant |
| Crospovidone[**] | q.s. | Disintegrant |
| Magnesium stearate[**] | q.s. | Lubricant/Antiadherent |
| Silicon dioxide[**] | q.s. | Adsorbent/Antiadherent |
| Talc[**] | q.s. | Lubricant/Antiadherent |
| Water[***] | 400 ml | Formulation basis |

[*]Used in the granulation of berberine and RY in Granules A
[**]The absolute and relative amounts of these excipients depend on the dimensions and shape of the compression punch, on the type of tablet press and on the system for loading the powders in the compression chamber of the tablet press.
[***]Water is used in the preparation of Granules A. The amount shown in the table is purely indicative and depends on the type and dimensions of the granulator employed. It is removed completely in the drying stage.

Example 2

Heat-Sealed Sachets Containing Powder for Extemporaneous Suspension

The formulation described below relates to active principles and excipients (with description of the corresponding technological function) that can be used in the formulation of a powder for the preparation of extemporaneous suspensions that are to be taken orally. The daily dose is incorporated in a single portion of powder contained in a heat-sealed sachet comprising a paper outer layer, an aluminium interlayer and a polyethylene inner layer.

The operations for preparation of the pharmaceutical form in question, which are well known and can be applied by a person skilled in the art, are essentially as follows.

Weighing of the individual components of the formulation.

Wet granulation, using aqueous solution of polyvinylpyrrolidone K-25, of berberine, RY and pregelatinized starch (granules A) in a suitable granulator.

Drying of granules A in an air-circulating stove at a temperature not above 50° C. and to constant weight (any other type of drying can be used provided it is validated beforehand).

Sieving of granules A and of the other components of the formulation.

Preparation of the Filling Mixture by Dry Homogenization of Granules A and of the Other components of the formulation in a suitable mixer.

Thermal forming of the sachets on a suitable automatic line.

Filling and sealing of the sachets on the same automatic line described above, finally obtaining sachets having the desired shape and dimensions and containing the monodose powder for extemporaneous use.

| Active principles | Quantity/tablet |
|---|---|
| Berberine dry extract[*] | 550 mg |
| (Corresponding to berberine) | (500 mg) |
| RY[**] | 200 mg |
| (Corresponding to monacoline K) | (3 mg) |
| Extract of microalgae[***] | 20 mg |
| (*Haematococcus purpureus*, corresponding to astaxanthin) | (0.5 mg) |
| Policosanol | 10 mg |
| Coenzyme Q10 | 2 mg |
| Folic acid | 0.2 mg |

[*]Contains 90% berberine
[**]Rice fermented with *Monascus purpureus* containing 1.5% of monacoline K
[***]Contains 2.5% astaxanthin

| Excipients | Quantity/sachet | Function |
|---|---|---|
| Sorbitol[*] | q.s. | Diluent/Sweetener |
| Citric acid[*] | q.s. | Flavour enhancer |
| Polyethylene Glycol 4000 | q.s. | Lubricant/Plasticizer |
| Others[**] | as desired | Sweeteners/Flavourings |

[*]The absolute and relative amounts of these excipients depend on the type of sachet-making machine used and on the dimensions of the sachets.
[**]Flavourings and sweeteners can be added freely, according to preferences.

REFERENCES

1. Benitez M, Romero C, Mas R et al.: A comparative study of policosanol versus pravastatin in patients with type II hypercholesterolemia. Curr Ther Res Clin Exp 1997; 58:859-867
2. Boushey C J, Beresford S A A, Omenn G S, Motulsky A G: A quantitative assessment of plasma homocysteine as a risk factor for vascular disease. Probable benefits of increasing folic acid intakes. JAMA 1995; 274:1049-1057
3. Cicero A F G, Laghi L, Setnikar I: A help to diet from active natural products. A pilot clinical study on lipid profile. In preparation 2006

4. Cureton K: The physiological effects of wheat germ oil in humans. 1972; In Exercise, Charles C Thomas, Springfield, Ill.—USA: 296-300
4. Patent application TO2004A000682 filed 7 Oct. 2004
5. Endo A: Chemistry, Biochemistry and Pharmacology of HMG-CoA reductase inhibitors. Klin Wochensr. 1988; 421-427
6. Folkers K, Langsjoen P, Willis R et al.: Lovastatin decreases coenzyme Q10 levels in humans. Proc Natl Acad Sci 1990; 87:8931-8934
7. Goumi-Berthold I, Goumi-Berthold H: Policosanol: clinical pharmacology and therapeutic significance of a new lipid-lowering agent. Am Heart J 2002; 143:356-365
8. Grigore L, Redaelli L, Maggi et al. Armolipid, a nutritional supplement, effectively reduces plasma total and LDL cholesterol in moderate hypercholesterolemia. Drugs Affecting Lipid Metabolism. Venice, October 2004, Abstract p. 131
9. Iwamoto T, Hosoda K, Hirano R, Kurata H, Matsumoto A, Miki W, Kamiyama M, Itakura H, Yamamoto S, Kondo K: Inhibition of low density lipoprotein oxidation by Astaxanthin. J Atheroscler Thromb 2000; 7:216-222
10. Kannel W B, Castelli W P, Gordon T et al. Lipoprotein cholesterol in the prediction of atherosclerotic disease: new perspectives based on the Framingham Heart Study. Ann Intern Med 1995; 90:85-91
11. Kong W, Wei J, Abidi P, Lin M, Inaba S, Li C, Wang Y, Wang Z, Si S, Pan H, Wang S, Wu J, Wang Y, Li Z, Liu J, Jiang J D: Berberine is a novel cholesterol-lowering drug working through a unique mechanism distinct from statins. Nat. Med. 2004; 10:1344-1351
12. Leung A Y, Foster S: Enciclopedia delle piante medicinali. Edizioni APORIE, Rome 1996, p. 203-205
13. Lockwood K, Moesgaard S, Hanioka T, Folkers K: Apparent partial remission of breast cancer in 'high risk' patients supplemented with nutritional antioxidants, essential fatty acids and coenzyme Q10. Molec Aspects Med 1994; 15:231-240
14. Lockwood K, Moesgaard S, Yamamoto T, Folkers K: Progress on therapy of breast cancer with vitamin Q10 and the regression of metastases. Biochem Biophys Res Commun 1995; 212:172-177
15. Longo N: In Harrison's 15th Edition. Mc Graw-Hill New York 2001, p. 2306
16. Lowe L P, Greenland P, Ruth K J et al.: Impact of major cardiovascular disease risk factors, particularly in combination, on 22-year mortality in women and men. Arch Intern Med 1998; 158:2007-2014
17. Man R Y, Lynn E G, Cheung F, Tsang P S.O.K.: Cholestin inhibits Cholesterol synthesis and secretion in hepatic cells (HepG2). Mol Cell Biochem. 2002; 233: 153-158
18. Menendez R, Amor A M, Rodeiro I et al.: Policosanol modulates HMG-CoA reductase activity in cultured fibroblasts. Arch Med Res 2001; 32:8-12
19. Menendez R, Amor M R, Gonzales R M et al.: Effects of Policosanol on the hepatic cholesterol biosynthesis of normocholesterolemic rats. Biol Res 1996; 29:253-257
20. Menendez R, Fernandez S I, Del Rio A et al.: Policosanol inhibits cholesterol biosynthesis and enhances low density lipoprotein processing in cultured human fibroblasts. Biol Res 1994; 27:199-203
21. Menendez R, Fraga V, Amor A M et al.: Oral administration of Policosanol inhibits in vitro copper ion-induced rat lipoprotein peroxidation. Physiol Behav 1999; 67:1-7
22. Menendez R, Mas R, Amor A M et al.: Effects of Policosanol treatment on the susceptibility of low density lipoprotein (LDL) isolated from healthy volunteers to oxidative modification in vitro. Br J Clin Pharmacol. 2000; 50:255-262
23. Ministero della Salute 2003: Linee guida europee sulla prevenzione della malattia cardiovascolare nella pratica clinica 2003. Italian version of the document "European guidelines on cardiovascular disease prevention in clinical practice. Third Joint Task Force of European and other Societies on cardiovascular disease prevention in clinical practice. Eur Heart J 2003; 24:1601-1610
24. Monographie *Berberis vulgaris* (Berberitze). Bundesanzeiger 1989; 43; 2.03.
25. Osservatorio Epidemiologico Cardiovascolare Italiano. Ital Heart J 2004; 5(Suppl 3):49S-92S
26. Schwartz L M, Woloshin S: Changing disease definitions: implications for disease prevalence (Analysis of the Third National Health and Nutrition Examination Survey, 1988-1994). Eff Clin Pract 1999; 2:76-85
27. Sempos C T, Ceeman J I, Carroll M D et al.: Prevalence of high blood cholesterol among US adults. An update based on guidelines from the second report of the National Cholesterol Education Program Adult Treatment Panel. JAMA 1993; 269:3009-3014
28. Senin P, Setnikar I, Rovati A L: Formulation for oral administration having a beneficial effect on the cardiovascular system. Patent application TO 2004 A 000682 Jul. 10, 2004
29. Setnikar I, Senin P, Rovati L C. (2005): Antiatherosclerotic efficacy of policosanol, red yeast rice extract and astaxanthin in the rabbit. ArzneimittelForschung 2005; 55:312-317
30. Steinberg D: Low density lipoprotein oxidation and its pathobiological significance. J Biol Chem 1997; 272: 20963-20966
31. Task Force. European guidelines on cardiovascular disease prevention in clinical practice. Third Joint Task Force of European and other Societies on cardiovascular disease prevention in clinical practice. Eur Heart J 2003; 24:1601-1610
32. Willis R A, Folkers K, Tucker J L et al.: Lovastatin decreases coenzyme Q10 levels in rats. Proc Natl Acad Sci 1990; 87:8928-8930

The invention claimed is:
1. A composition for oral administration having a beneficial effect on the cardiovascular system, comprising as active principles policosanol, red yeast and astaxanthin, characterized in that it further comprises berberine or an extract containing berberine.
2. The composition according to claim 1, characterized in that it comprises, as a source of astaxanthin, an extract of microalgae.
3. The composition according to claim 1, characterized in that it further comprises coenzyme Q10.
4. The composition according to claim 1, in the form of a unit dose, ready for the administration of berberine at a daily dose from 250 to 1000 mg.
5. The composition according to claim 1, in the form of a unit dose, ready for the administration of policosanol at a daily dose from 5 to 40 mg.
6. The composition according to claim 5, in the form of a unit dose, ready for the administration of policosanol at a daily dose from 10 to 20 mg.
7. The composition according to claim 1, in the form of a unit dose, ready for the administration of red yeast at a daily dose corresponding to 1-6 mg of monacoline.

8. The composition according to claim 1, in the form of a unit dose, ready for the administration of astaxanthin at a daily dose from 0.1 to 5 mg.

9. The composition according to claim 1, in the form of a unit dose, comprising coenzyme Q10 and ready for the administration of coenzyme Q10 at daily doses from 1 to 20 mg.

10. The composition according to claim 1, in the form of tablets, capsules or powder for extemporaneous suspension.

11. A method for normalizing homocysteinaemia or protecting vasal endothelium comprising administering to a subject in need thereof, an effective amount of the composition according to claim 1.

12. A method for the treatment of hypercholesterolaemia or hypertriglyceridaemia comprising administering to a subject in need thereof, an effective amount of the composition according to claim 1.

13. The composition according to claim 2, wherein the source of astaxanthin is *Haematococcus purpureus*.

14. The composition according to claim 7, in the form of a unit dose, ready for the administration of red yeast at a daily dose corresponding to 1-3 mg of monacoline.

15. The composition according to claim 8, in the form of a unit dose, ready for the administration of astaxathin at a daily dose of from 0.4 to 2 mg.

16. The composition according to claim 9, in the form of a unit dose, ready for administration of coenzyme Q10 at a daily dose of 1 to 4 mg.

17. A composition for oral administration having a beneficial effect on the cardiovascular system, comprising as active principles policosanol, red yeast and astaxanthin, characterized in that it further comprises berberine or an extract containing berberine, wherein policosanol is at a daily dose from 5 to 40 mg; berberine is at a daily dose from 250 to 1000 mg; and red yeast is at a daily dose corresponding to 1-6 mg of monacoline.

* * * * *